United States Patent [19]

Yamada et al.

[11] Patent Number: 5,449,442
[45] Date of Patent: Sep. 12, 1995

[54] CLEANING AND DISINFECTING METHOD FOR CONTACT LENS

[75] Inventors: Kenji Yamada; Hideaki Kamiya, both of Nagoya, Japan

[73] Assignee: Tomey Technology Corporation, Nagoya, Japan

[21] Appl. No.: 314,806

[22] Filed: Sep. 29, 1994

[30] Foreign Application Priority Data

Oct. 1, 1993 [JP] Japan .................. 5-247203

[51] Int. Cl.$^6$ .................. C25B 1/00; C11D 7/42
[52] U.S. Cl. .................. 204/130; 204/131; 204/95; 204/103
[58] Field of Search .................. 204/130, 131, 95, 103

[56] References Cited

U.S. PATENT DOCUMENTS

| | | | |
|---|---|---|---|
| 2,898,282 | 8/1959 | Flook, Jr. et al. | 204/195 |
| 4,202,740 | 5/1980 | Stoner et al. | 204/130 |
| 4,384,943 | 5/1983 | Stoner et al. | 204/149 |
| 4,396,583 | 8/1983 | LeBoeuf | 422/301 |
| 4,568,517 | 2/1986 | Kaspar et al. | 422/30 |
| 4,732,185 | 3/1988 | Cowle et al. | 134/84 |
| 4,761,208 | 8/1988 | Gram et al. | 204/95 |
| 4,836,859 | 6/1989 | Konishi et al. | 134/1 |
| 4,839,004 | 6/1989 | Castellini | 204/128 |
| 4,921,544 | 5/1990 | Cowle et al. | 134/1 |
| 4,954,263 | 9/1990 | Woodhouse | 210/695 |
| 5,118,401 | 6/1992 | Oksman et al. | 204/228 |
| 5,129,999 | 7/1992 | Holland et al. | 204/131 |
| 5,135,623 | 8/1992 | Dziabo et al. | 204/101 |
| 5,246,552 | 9/1993 | Kamiya et al. | 204/131 |

FOREIGN PATENT DOCUMENTS

| | | |
|---|---|---|
| 56-68454 | 6/1981 | Japan . |
| 57-153653 | 9/1982 | Japan . |
| 60-7060 | 3/1985 | Japan . |
| 60-217333 | 10/1985 | Japan . |
| 63-35023 | 3/1988 | Japan . |
| 63-193129 | 8/1988 | Japan . |
| 3-171032 | 7/1991 | Japan . |
| WO89/00430 | 1/1989 | WIPO . |

*Primary Examiner*—John Niebling
*Assistant Examiner*—Arun S. Phasge
*Attorney, Agent, or Firm*—Armstrong, Westerman, Hattori, McLeland & Naughton

[57] ABSTRACT

A cleaning and disinfecting method for a contact lens comprising immersing a contact lens in a treating solution containing a hypohalogenous acid and applying a direct current to the treating solution with repeatedly reversing a positive electrode and a negative electrode plural times, or comprising immersing a contact lens in a solution for treatment containing a halide and applying a direct current to the solution for treatment with repeatedly reversing a positive electrode and a negative electrode plural times. According to the cleaning and disinfecting methods, a contact lens can be cleaned up and disinfected by excellent disinfecting ability and cleaning ability of the hypohalogenous acid, and after that, the hypohalogenous acid can be immediately reduced and detoxicated.

7 Claims, 9 Drawing Sheets

CLEANING AND DISINFECTING METHOD FOR CONTACT LENS

BACKGROUND OF THE INVENTION

The present invention relates to a cleaning and disinfecting method for a contact lens, and more particularly to a cleaning and disinfecting method for a contact lens, which detoxicates a hypohalogenous acid in a short period of time after showing excellent cleaning and disinfecting effects of the hypohalogenous acid.

A contact lens has some apprehensions that eyes are injured when the contact lens is continuously worn in eyes as it is for a long period of time because stains in the surroundings, microbes, proteins contained in tear fluid, and the like adhere to the contact lens while the contact lens is worn in eyes. Accordingly, there is a necessity to clean up or disinfect the contact lens regularly, preferably every day.

As a cleaning method for a contact lens, a method comprising washing the contact lens with a solution containing a surface active agent by fingers has been conventionally known, and according to this method, stains on the surface of the contact lens can be removed. However, for instance, when the method is applied to a hard contact lens, there is an apprehension that the hard contact lens is broken or damaged during washing. Also, when the method is applied to a water-absorptive soft contact lens, stains such as proteins, which are incorporated in the contact lens, cannot be completely removed.

Also, as a cleaning method for regenerating and reusing a contact lens stained with proteins, a method comprising using a cleaning agent containing a proteolytic enzyme has been conventionally known. When this cleaning method is used, although proteins adhered to the surface of the contact lens can be decomposed, it takes a long period of time to decompose proteins because the enzyme is used. Especially, when a water-absorptive soft contact lens is cleaned up by using the cleaning agent, besides taking a longer period of time for treating the water-absorptive soft contact lens in comparison with the period of time for treating a hard contact lens, sufficient removing effects of proteins cannot be expected because the proteolytic enzyme itself should be incorporated in a contact lens so that proteins being denatured in the internal of the contact lens can be decomposed.

U.S. Pat. No. 4,732,185 discloses a cleaning method for a contact lens comprising establishing an electric field in a determined direction in a boric acid-EDTA buffer solution having pH 8 to 9 and immersing a contact lens in the solution to remove proteins from the contact lens by electrophoresis. When this method is carried out, proteins incorporated in a water-absorptive contact lens can be surely removed. However, the method requires that proteins should not be denatured and are ionized, and there are some problems in the method such that it takes a long period of time for the treatment.

On the other hand, as a disinfecting method for a water-absorptive contact lens, there have been known a method comprising immersing a contact lens in aqueous hydrogen peroxide to disinfect the contact lens and decomposing hydrogen peroxide with a metallic catalyst, a reducing agent and an enzyme catalyst to detoxicate the solution, a disinfecting method comprising making use of a compound such as chlorhexidine, and the like.

However, according to the above-mentioned method of using aqueous hydrogen peroxide, besides taking a long period of time for the treatment since hydrogen peroxide remaining in the water-absorptive soft contact lens should be decomposed, stimulation such as smarting of eyes occurs if hydrogen peroxide remaining in the internal of the water-absorptive contact lens is not completely decomposed. Therefore, the above method is not a suitable method for disinfecting a water-absorptive contact lens. Also, according to the above-mentioned disinfecting method of using a compound such as chlorhexidine, there is a danger such that the compound is adsorbed to the lens or allergosis against eyes occurs by the remaining compound.

On the other hand, by using a disinfecting method comprising using hypochlorous acid, pathogen in eyes such as *Staphylococcus aureus, Escherichia coli, Pseudomonas aeruginosa* or *Candida albicans* can be disinfected with hypochlorous acid in a concentration of several ppm in a short period of time, and stains of organic substances such as proteins adhered to the lens can be removed.

As a method comprising using hypochlorous acid, Japanese Unexamined Patent Publication No. 68454/1981 discloses a method comprising generating hypochlorous acid by electrolysis to disinfect a contact lens. However, according to this method, a contact lens should be immersed in a hypochlorous acid solution for a long period of time since it takes a long period of time to naturally dissipate hypochlorous acid remaining after the treatment. Therefore, when the method is used, there are problems such that color of the contact lens is decolored and that a mark printed on the contact lens is discolored.

A method comprising inactivating hypochlorous acid remained after a disinfecting treatment by using a suitable metallic catalyst or a suitable reducing agent has been proposed because a lens disinfected by using hypochlorous acid cannot be worn in eyes as it is. As the above-mentioned method, for instance, there have been known a method comprising reducing and detoxicating hypochlorous acid with a metallic catalyst as described in Japanese Unexamined Patent Publication No. 19218/1993, a method comprising reducing and detoxicating hypochlorous acid with a reducing agent as described in Japanese Unexamined Patent Publication No. 106492/1975 and Japanese Unexamined Patent Publication No. 1.90214/1992, and the like.

Several problems occur when hypochlorous acid is reduced after a disinfecting treatment using the method described above. The reduction procedures themselves are complicated, and aspectic conditions are difficult to maintain. Also, when the reduction procedures are not carried out exactly as instructed, the disinfected contact lenses may cause injury to the eyes of the wearer. And since the lenses are exposed to a high concentration of hypochlorous for an extended period of time while the hypochlorous acid is being reduced, deterioration of the lens or the fading of a colored lens may occur.

Japanese Unexamined Patent Publication No. 2544 16/1988 and Japanese Unexamined Patent Publication No. 254417/1988 propose a method comprising separating an electrolyte solution in a cleaning bath into two rooms by a diaphragm to which an ion-exchange membrane is applied, applying a direct current to the electrolyte solution to generate an acid solution containing hypochlorous acid and an alkali solution, cleaning a contact lens in the alkali solution and applying an electric current in reverse to the electrolyte solution to neutralize the alkali solution in which the contact lens is immersed. However, according to the method, although pH of the alkali solution in which the contact lens is immersed becomes neutral, the generated hypochlorous acid is not reduced and remains in the solution, so that there is a problem that the contact lens cannot be worn in eyes as it is after the treatment.

The present invention has been accomplished in consideration of the above prior art.

An object of the present invention is to provide a cleaning and disinfecting method for a contact lens, which cleans up and disinfects a contact lens with excellent disinfecting activities and excellent cleaning activities of a hypohalogenous acid, and detoxicates the hypohalogenous acid in a short period of time.

Another object of the present invention is to provide an electrical treating method for a contact lens, which heightens electrical safety against an electric shock and an electric leakage by lowering electric power as much as possible, and can be preferably used for a treating apparatus for a contact lens which is convenient for carrying by using an electric cell, a battery, and the like.

These and other objects of the present invention will become apparent from the description hereinafter.

SUMMARY OF THE INVENTION

In accordance with the present invention, there is provided ① a cleaning and disinfecting method for a contact lens comprising immersing a contact lens in a treating solution containing a hypohalogenous acid and applying a direct current to the treating solution with repeatedly reversing a positive electrode and a negative electrode plural times, and ② a cleaning and disinfecting method for a contact lens comprising immersing a contact lens in a solution for treatment containing a halide and applying a direct current to the solution for treatment with repeatedly reversing a positive electrode and a negative electrode plural times.

DETAILED DESCRIPTION

Figure 1:
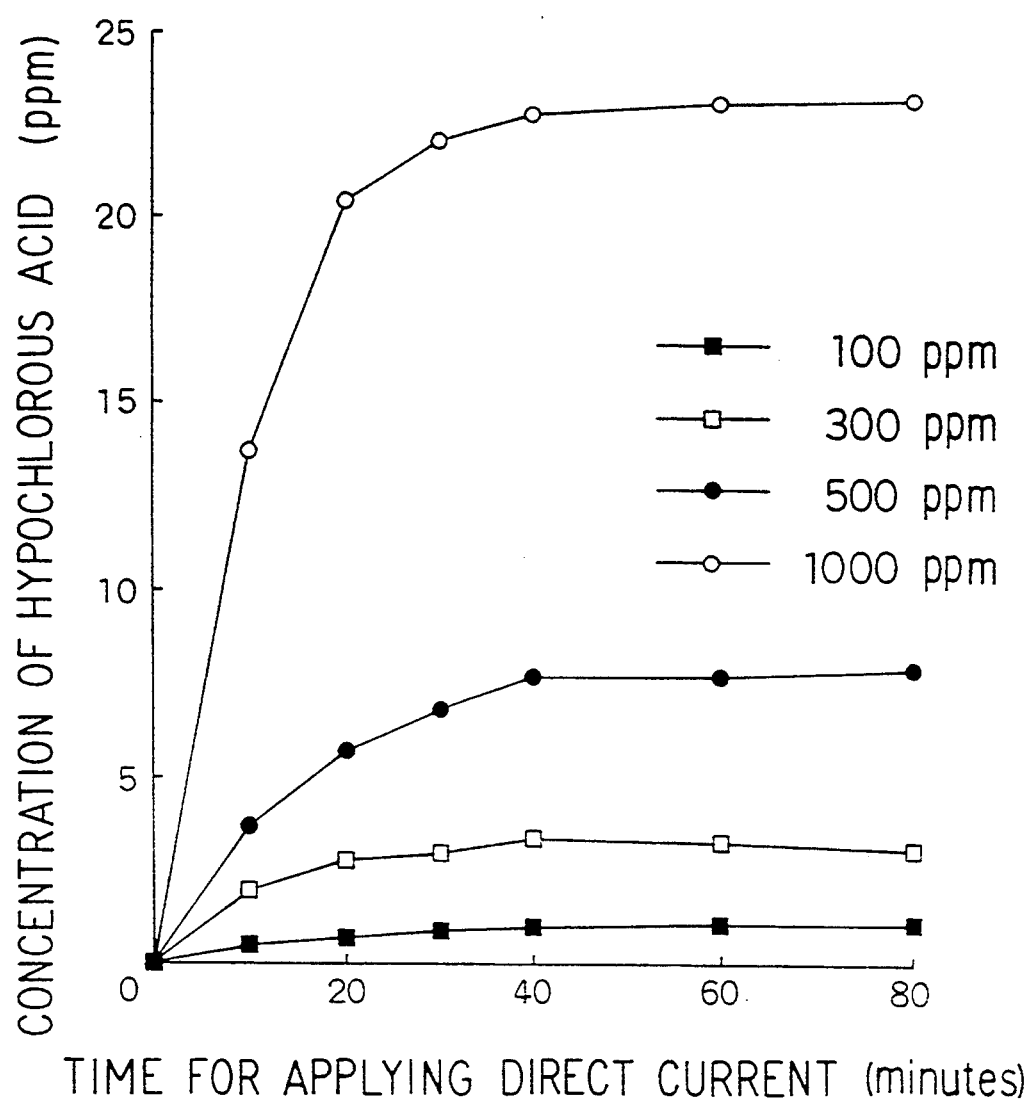
FIG. 1 is a graph showing the relation between time for applying direct current and concentration of hypochlorous acid in the solution containing a halide according to Experimental Example 1.

The cleaning and disinfecting method for a contact lens of the present invention (hereinafter referred to as First Invention) comprises, as mentioned above, immersing a contact lens in a treating solution containing a hypohalogenous acid and applying a direct current to the treating solution with repeatedly reversing a positive electrode and a negative electrode plural times.

Moreover, the cleaning and disinfecting method for a contact lens of the present invention (hereinafter referred to as Second Invention) comprises, as mentioned above, immersing a contact lens in a solution for treatment containing a halide and applying a direct current to the solution for treatment with repeatedly reversing a positive electrode and a negative electrode plural times.

In the present invention, a hypohalogenous acid is intended to mean an oxygen acid containing a halogen having an oxidation number of $+1$, which is represented by the general formula: HXO wherein X is Cl or Br. Therefore, the hypohalogenous acid contains a hypohalogeneous acid ion, i.e. hypohalogenite ion $(XO^-)$.

First of all, the First Invention is explained below.

In the First Invention, cleaning and disinfecting effects of the hypohalogenous acid are availed and after that, the hypohalogenous acid can be detoxicated in a short period of time.

The treating solution used in the cleaning and disinfecting method of the present invention contains a hypohalogenous acid. As the hypohalogenous acid, hypochlorous acid and hypobromous acid can be cited.

It is preferable that the concentration of the hypohalogenous acid in the treating solution is 0.1 to 1000 ppm. When the concentration of the hypohalogenous acid is higher than 1000 ppm, there is a tendency that there occurs an apprehension such that a contact lens in the treating solution is damaged. Also, when the concentration of the hypohalogenous acid is lower than 0.1 ppm, there is a tendency that cleaning and disinfecting effects of the hypohalogenous acid is difficult to be sufficiently revealed. When only a disinfecting treatment for the contact lens is carried out, it is preferable that the concentration of the hypohalogenous acid in the treating solution is about 2 to about 10 ppm. Also, when a disinfecting treatment and a cleaning treatment against stains of organic substances such as proteins are carried out, it is preferable that the concentration of the hypohalogenous acid in the treating solution is at least about 20 ppm.

As a method for preparing a treating solution containing the hypohalogenous acid, there can be cited, for instance, a method comprising adding a hypohalogenous acid salt such as sodium hypochlorite, sodium hypobromite, potassium hypochlorite or potassium hypobromite to water, and the like. In the present invention, when the above-mentioned method for preparing the treating solution is employed, usually, after the treating solution containing the hypohalogenous acid is prepared, a contact lens is immersed in the obtained treating solution. Also, in the present invention, the hypohalogenous acid salts may be added to water in which a contact lens is previously immersed.

Furthermore, in the First Invention, in order to prepare a treating solution containing the hypohalogenous acid, besides the above-mentioned method, there can be cited, for instance, a method comprising applying a direct current to a solution prepared by adding a halide to water, and the like. As the halide, there can be cited, for instance, chlorides such as sodium chloride and potassium chloride, bromides such as sodium bromide and potassium bromide, and the like. It is preferable that the concentration of the halide in the solution, the voltage and the applying period of time of direct current are respectively adjusted so that the concentration of the generated hypohalogenous acid in the treating solution is within the above-mentioned range. For instance, it is desired that the concentration of the halide in the solution is 10 to 3000 ppm, preferably 100 to 1500 ppm. Also, it is preferable that the voltage when applying a direct current is about 1.5 to about 20 V, and the applying period of time of the direct current is about 30 seconds to about 30 minutes. When the concentration of the halide is lower than 10 ppm, there is a tendency that cleaning and disinfecting effects of the hypohalogenous acid is difficult to be sufficiently revealed because the concentration of the generated hypohalogenous acid in the treating solution is too low. Also, when the concentration of the halide is higher than 3000 ppm, there is a tendency that it takes a long period of time to reduce and detoxicate the generated hypohalogenous acid.

When the above-mentioned method is employed, usually, after a direct current is applied to a treating solution, a contact lens is immersed in the treating solution. However, a direct current may be applied to a solution containing the halide in which a contact lens is previously immersed.

In the First Invention, cleaning and disinfecting of a contact lens are carried out by immersing a contact lens in the above treating solution and applying a direct current to the treating solution with repeatedly reversing a positive electrode and a negative electrode plural times. The treating period of time is not particularly limited and can be adjusted according to the concentration of the hypohalogenous acid in the treating solution, the electric current, and the like. It is desired that the treating period of time is, generally, about 0 seconds to about 200 minutes, preferably about 30 seconds to about 30 minutes.

In the First Invention, when the direct current is applied to the treating solution in which a contact lens is immersed with repeatedly reversing the positive electrode and the negative electrode plural times, as an electrode material, it is preferable to use a material having a small ionization tendency because electrodes made of the material are hardly dissolved in the treating solution during electrolysis. Typical examples of the electrode material are, for instance, noble metals such as gold and platinum, a synthetic resin or ceramic on which a noble metal such as gold or platinum is coated by plating or vapor deposition, and the like.

The reverse of the positive electrode and the negative electrode is repeatedly carried out, and it is desired that the interval of time for reversing is adjusted to from 0.01 second to 2 minutes, preferably from 0.1 to 30 seconds. When the interval of time for reversing is shorter than 0.01 second, there is a tendency that effects of electrophoresis become small, and that deterioration of electrodes such that the electrodes are dissolved in the treating solution during the application of electric current to the treating solution because the change of polarity of electrodes is violenty carried out. Also, when the interval of time for reversing is longer than 2 minutes, there is a tendency that it takes a long period of time to reduce and detoxicate the hypohalogenous acid.

It is desired that the number of reversing the positive electrode and the negative electrode is 2 to 10000 times, preferably 10 to 6000 times, more preferably 15 to 100 times. When the number of reversing the positive electrode and the negative electrode is less than 2 times, there is an apprehension that the hypohalogenous acid is not completely reduced and detoxicated. Also, when the number of reversing the positive electrode and the negative electrode is more than 10000 times, the applying period of time of direct current becomes long, so that a contact lens in the treating solution tends to be thermally deteriorated because of the increase of temperature of the treating solution.

As a means for reversing the positive electrode and the negative electrode when the direct current is applied, there is no particular limitation, and for instance, a method comprising using an oscillator and a reverse circuit in which a counter frequency divider and a relay are used, a method comprising using a relay only, and the like can be cited.

The electric current applied to the treating solution is suitably selected depending upon the kinds of the treating solution, the area of the electrode, and the like. It is desired that, the electric current is usually within the range of about 0.001 to about 1 A, preferably about 0.01 to about 0.3 A. When the electric current is less than 0.001 A, there is a tendency that it takes a long period of time to reduce the hypohalogenous acid. Also, when the electric current exceeds 1 A, the temperature of the treating solution increases, so that there is an apprehension that thermal deterioration such as deformation of a hard contact lens or deterioration of a material of a contact lens having a high water content is caused when these contact lenses are cleaned up and disinfected, and also, there is a tendency that electrical safety such as no electric shock and no electric leakage is lowered because higher voltage is necessitated for giving a desired electric current.

It is desired that the voltage is about 1 to about 40 V, preferably about 1.5 to about 20 V when the direct current is applied between the electrodes. When the voltage is lower than 1 V, there is a tendency that there occur problems such that cleaning and disinfecting effects are lowered and that it takes a long period of time to reduce the hypohalogenous acid. Also, when the voltage exceeds 40 V, the temperature of the treating solution becomes higher than necessitated, so that there is an apprehension that a contact lens is thermally deteriorated during cleaning and disinfecting of the contact lens, and there is a tendency that electrical safety such as no electric shock and no electric leakage is lowered.

It is preferable that the applying period of time of the direct current to the treating solution with repeatedly reversing the positive electrode and the negative electrode plural times is longer than a necessary period of time to reduce and detoxicate a hypohalogenous acid in the treating solution. From the viewpoint of safety, it is more preferable that the applying period of time of the direct current is about 30 seconds to about 30 minutes.

Next, the Second Invention is explained below.

In the Second Invention, as mentioned above, by immersing a contact lens in a solution for treatment containing a halide and applying a direct current to the above solution for treatment with repeatedly reversing a positive electrode and a negative electrode plural times, a hypohalogenous acid can be generated, and moreover, the contact lens can be cleaned up and disinfected and the hypohalogenous acid can be reduced and detoxicated at the same time.

The solution for treatment used in the cleaning and disinfecting method of the Second Invention contains a halide. As concrete examples of the halide, for instance, chlorides such as sodium chloride and potassium chloride, bromides such as sodium bromide and potassium bromide, and the like can be cited.

It is desired that the concentration of the halide in the solution for treatment is 10 to 3000 ppm, preferably 100 to 1500 ppm. When the concentration of the halide is lower than 10 ppm, the concentration of the generated hypohalogenous acid in the solution for treatment becomes low, so that there is a tendency that cleaning and disinfecting effects of the hypohalogenous acid are difficult to be sufficiently revealed. Also, when the concentration of the halide is higher than 3000 ppm, there is a tendency that it takes a long period of time to reduce and detoxicate the generated hypohalogenous acid.

As a method for preparing a solution for treatment containing the halide, for instance, a method comprising adding the halide to water and adjusting the concentration of the halide so as to be included within the above-mentioned range can be cited.

In the Second Invention, the conditions when a contact lens is immersed in the solution for treatment and cleaned up and disinfected, can be the same as in the First Invention.

Also, in the Second Invention, after a contact lens is immersed in the solution for treatment, direct current may be previously applied to the solution for treatment to generate a hypohalogenous acid. It is preferable that the voltage, the applying period of time of direct current and the like are respectively adjusted so that the concentration of the generated hypohalogenous acid in the solution for treatment is within the range of 0.1 to 1000 ppm. For instance, it is preferable that the voltage when the direct current is applied is about 1.5 to about 20 V, and that the applying period of time of direct current is about 30 seconds to about 30 minutes.

If necessary, for instance, a buffering agent, an electrolyte, and the like can be suitably added to the treating solution and the solution for treatment used in the above-mentioned First Invention and the above-mentioned Second Invention.

The buffering agent can be used in order to stabilize pH of the treating solution or the solution for treatment. It is preferable that pH of the treating solution or the solution for treatment is adjusted to a physiologically isotonic value of about 6 to about 7.5 by using the buffering agent. As the buffering agent, for instance, a phosphoric acid salt, a boric acid salt and the like are exemplified, and these can be used alone or in admixture thereof. It is desired that the concentration of the buffering agent in the treating solution or the solution for treatment is adjusted to, usually, at most 0.2 mol/l, preferably from 0.0001 to 0.05 mol/l. When the concentration of the buffering agent exceeds 0.2 mol/l, for instance, in case that the buffering agent is used together with the following electrolyte, the total concentration of the buffering agent and the electrolyte in the treating solution or the solution for treatment increases and thereby the osmotic pressure of the treating solution or the solution for treatment becomes too high, so that there is a tendency that eyes are stimulated when a contact lens is cleaned up and disinfected in the treating solution or the solution for treatment and then the cleaned up and disinfected contact lens is worn in eyes as it is.

The electrolyte can be used in order to heighten the electric conductivity of the treating solution or the solution for treatment and adjust the osmotic pressure thereof.

As the electrolyte, for instance, sodium sulfate, sodium carbonate, sodium phosphate, sodium nitrate, calcium carbonate, calcium sulfate, potassium sulfate, and the like are exemplified, and these can be used alone or in admixture thereof. It is preferable that the concentration of the electrolyte in the treating solution or the solution for treatment is adjusted so that the osmotic pressure of the treating solution or the solution for treatment is within a range of 250 to 350 mmol/kg when the electrolyte is used together with the above-mentioned buffering agent.

In the cleaning and disinfecting method of the present invention, for instance, the treating solution containing a hypohalogenous acid or the solution for treatment containing a halide is prepared by such a manner as mentioned above, and a contact lens is immersed in the treating solution or the solution for treatment, and then a direct current is applied to the treating solution or the solution for treatment with repeatedly reversing the positive electrode and the negative electrode plural times to generate a peroxide, and the resulting hypohalogenous acid in the solution is reduced and detoxicated.

When a conventional method comprising applying a direct current to a solution without repeatedly reversing a positive electrode and a negative electrode during the treatment is carried out, the concentration of the hypohalogenous acid in the solution becomes stable and constant at a certain concentration. To the contrary, according to the cleaning and disinfecting method of the present invention, a hypohalogenous acid having a sufficient concentration for cleaning and disinfecting a contact lens can be completely reduced and detoxicated in the treating solution or the in the solution for treatment in a short period of time such as for several minutes to several tens of minute.

In the cleaning and disinfecting method of the present invention, in order to sufficiently remove stains such as lipid adhered to a contact lens, a surface active agent may be added to the treating solution or the solution for treatment before the contact lens is immersed in the treating solution or the solution for treatment, or the contact lens may be cleaned up in a cleaning solution containing a surface active agent after the contact lens is cleaned up and disinfected.

As the surface active agent, for instance, anionic surface active agents such as surfuric acid esters of higher alcohols and liquid fatty oil, alkyl ether sulfuric acid esters, alkyl sulfonates, sulfosuccinates and alkyl ether sodium sulfonates; cationic surface active agents such as alkyl amine salts and alkyl ammonium salts;

nonionic surface active agents such as alkyl ethers, alkyl phenyl ethers, polyoxypropylene ethers, alkyl ester glycerine fatty acid esters, sorbitan fatty acid esters and polyoxyethylene sorbitan fatty acid esters, and the like are exemplified, and these can be used alone or in admixture thereof.

When the surface active agent is used by including in the treating solution or the solution for treatment, a surface active agent which does not react with a resulting hypohalogenous acid can be used, and as this surface active agent, for instance, alkyl ether sodium sulfonates and the like can be preferably exemplified. Also, when the concentration of the surface active agent is too high, excess bubbles are generated in the treating solution or the solution for treatment, and sometimes flow out from the vessel because of gas generated by the electrode reaction. Accordingly, it is desired that the concentration of the surface active agent in the treating solution or the solution for treatment is at most 0.1% by weight, preferably at most 0.05% by weight.

Also, when stains of proteins such as denaturated proteins which are difficult to be removed are existed in the internal of a contact lens, the contact lens may be touched with a solution containing a proteolytic enzyme before subjecting the contact lens to the cleaning and disinfecting treatment so that the denaturated proteins can be easily removed.

As the proteolytic enzyme, for instance, vegetable proteolytic enzymes and aminal proteolytic enzymes such as papain, chymopapain, pancreatin, trypsin, chymotrypsin, pepsin, ficin, carboxypeptidase, aminopeptidase and bromelin; proteolytic enzymes derived from microbes such as Bacillus, Streptomyces bacteria and Aspergillus mold, and the like are exemplified, and these can be used alone or in admixture thereof. It is preferable that the concentration of the proteolytic enzyme in the treating solution or the solution for treatment is adjusted so that the enzyme activity of the proteolytic enzyme in the treating solution or the solution for treatment becomes within a range of 300 to 1000 units/ml.

After cleaning up and disinfecting a contact lens, the hypohalogenous acid generated in the treating solution or the solution for treatment is reduced and detoxicated by applying a direct current to the treating solution or the solution for treatment with repeatedly reversing a positive electrode and a negative electrode plural times, and then the cleaned and disinfected contact lens can be taken out from the treating solution or the solution for treatment and worn in eyes as it is.

In the present invention, it is preferable that the First Invention comprising immersing a contact lens in the treating solution containing the hypohalogenous acid and applying a direct current to the treating solution with reversing electrodes is employed from the viewpoint that the concentration of the hypohalogenous acid in the treating solution can be particularly stable. Also, it is preferable that the Second Invention comprising immersing a contact lens in the solution for treatment not containing the hypohalogenous acid but containing the halide, generating a hypohalogenous acid, for instance, by applying a direct current to the solution for treatment to generate a hypohalogenous acid and then applying a direct current to the solution for treatment with reversing electrodes is employed from the viewpoint of safety of the solution before the treatment.

Because the cleaning and disinfecting effects of the hypohalogenous acid for a contact lens would appear in a short period of time, after the contact lens is cleaned up and disinfected, it is preferable that the hypohalogenous acid is reduced as soon as possible from the viewpoint of the prevention of the contact lens from damage.

As mentioned above, for instance, when a conventional method of using a reducing agent is carried out, it takes a long period of time to reveal the effects of the reducing agent after the cleaning and disinfecting treatment is completed. When a conventional method of using a reducing catalyst is carried out, it takes a long period of time to reduce the hypohalogenous acid. Accordingly, these conventional methods have a problem that the contact lens is greatly damaged becasue the contact lens is continuously immersed in the solution containing the hypohalogenous acid whose concentration remains high for a period of time longer than necessitated until the reduction of the hypohalogenous acid is completed. To the contrary, in the present invention, a direct current can be applied to the treating solution or the solution for treatment with controlling electric current by setting up the period of time by using a timer and the like in accordance with the kinds of the treating solution or the solution for treatment, so that the hypohalogenous acid can be reduced and detoxicated in an extremely short period of time after the cleaning and disinfecting treatment is carried out. Accordingly, as to the cleaning and disinfecting method of the present invention, the contact lens is not damaged.

Moreover, in the present invention, complicated steps are not necessitated after the cleaning and disinfecting treatment, and the cleaned and disinfected contact lens can be taken out from the treating solution or the solution for treatment and worn in eyes as it is. Therefore, the aseptic condition of the contact lens can be maintained in the extremely excellent state. Accordingly, the method of the present invention is extremely available as the cleaning and disinfecting method for a contact lens.

As mentioned above, according to the cleaning and disinfecting method for a contact lens of the present invention, the contact lens can be cleaned up and disinfected by excellent cleaning and disinfecting effects of the hypohalogenous acid, and the hypohalogenous acid can be reduced and detoxicated in a short period of time.

The cleaning and disinfecting method for a contact lens of the present invention is more specifically described and explained by means of the following Examples. It is to be understood that the present invention is not limited to the Examples, and various changes and modifications may be made in the invention without departing from the spirit and scope thereof.

EXPERIMENTAL EXAMPLE 1

To a solution of pH 7 containing sodium sulfate in a content of $1.1 \times 10^{-1}$ mol/l, sodium phosphate in a content of $2.4 \times 10^{-4}$ mol/l and disodium phosphate in a content of $3.5 \times 10^{-4}$ mol/l, sodium chloride was added so as to adjust the concentration of sodium chloride to 100 ppm, 300 ppm, 500 ppm or 1000 ppm.

Each 7 ml of the solutions was put into a treating vessel equipped with a pair of electrodes of ceramic plated with platinum and having an area of 0.21 cm$^2$ and an interval of the electrodes of 4 mm.

A direct current having DC voltage of 5 V was applied to each of the solutions to measure the generated amount of hypochlorous acid with the passage of time. The results are shown in FIG. 1. The concentration of residual hypochlorous acid in the solutions was measured in accordance with the standard methods for the examination of water (a quantitative method of o-tolidine) described in Standard Methods of Analysis for Hygienic Chemists —With Commentary— authorized by the Pharmaceutical Society of Japan (1990) Kanehara & Co., Ltd., p.949.

As is clear from the results shown in FIG. 1, it can be seen that the generated amount of hypochlorous acid could be stabilized when a direct current was applied to the solution containing a halide.

EXPERIMENTAL EXAMPLE 2

To a solution of pH 7 containing sodium sulfate in a content of $1.1 \times 10^{-1}$ mol/l, boric acid in a content of $1.0 \times 10^{-4}$ mol/l and borax in a content of $8.0 \times 10^{-6}$ mol/l, sodium chloride was added so as to adjust the concentration of sodium chloride to 100 ppm, 300 ppm, 500 ppm or 1000 ppm.

Each 7 ml of the solutions was put into a treating vessel equipped with a pair of electrodes of ceramic plated with platinum and having an area of 0.21 cm² and an interval of the electrodes of 4 mm.

A direct current having DC voltage of 5 V was applied to each of the solutions to measure the generated amount of hypochlorous acid with the passage of time in the same manner as in Experimental Example 1. As a result, the generated amount of hypochlorous acid in each of these solutions was the same as that shown in FIG. 1.

EXPERIMENTAL EXAMPLE 3

To a solution of pH 7 containing potassium sulfate in a content of $1.1 \times 10^{-1}$ mol/l, boric acid in a content of $1.0 \times 10^{-4}$ mol/l and borax in a content of $8.0 \times 10^{-6}$ mol/l, sodium chloride was added so as to adjust the concentration of sodium chloride to 100 ppm, 300 ppm, 500 ppm or 1000 ppm.

Each 7 ml of the solutions was put into a treating vessel equipped with a pair of electrodes of ceramic plated with platinum and having an area of 0.21 cm² and an interval of the electrodes of 4 min.

A direct current having DC voltage of 5 V was applied to each of the solutions to measure the generated amount of hypochlorous acid with the passage of time in the same manner as in Experimental Example 1. As a result, the generated amount of hypochlorous acid in each of these treating solutions was the same as that shown in FIG. 1.

EXPERIMENTAL EXAMPLE 4

Each 7 m g of the solutions used in Experimental Example 1 was put into a treating vessel equipped with a pair of electrodes of ceramic plated with platinum and having an area of 0.21 cm² and an interval of the electrodes of 4 min.

A direct current having DC voltage of 5 V was applied to each of the solutions for 20 minutes to generate hypochlorous acid. Then, to each of the solutions, a direct current having DC voltage of 5 V and a current of 0.04 A was applied with repeatedly reversing the positive electrode and the negative electrode at an interval of time of 7.5 seconds by using a reverse circuit. The change of the concentration of hypochlorous acid was measured with the passage of time. The results are shown in FIG. 2.

Figure 2:
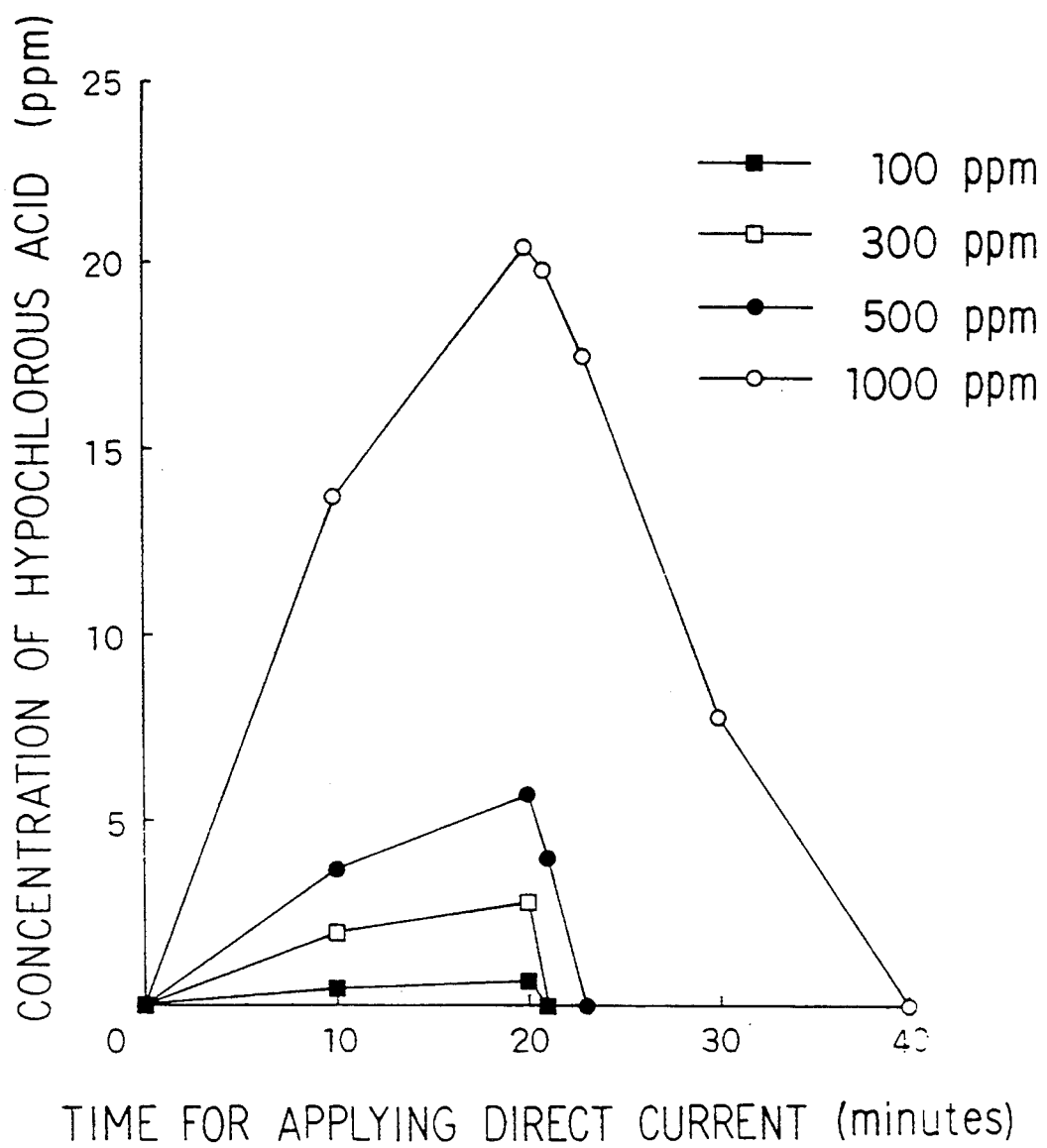
FIG. 2 is a graph showing the relation between time for applying direct current and concentration of hypochlorous acid in the solution containing a halide according to Experimental Example 4.

As is clear from the results shown in FIG. 2, it can be seen that hypochlorous acid was reduced in a short period of time when the positive electrode and the negative electrode were repeatedly reversed.

EXPERIMENTAL EXAMPLE 5 AND COMPARATIVE EXPERIMENTAL EXAMPLE 1

To a solution of pH 7 containing sodium sulfate in a content of $1.1 \times 10^{-1}$ mol/l, sodium phosphate in a content of $2.4 \times 10^{-4}$ mol/l and disodium phosphate in a content of $3.5 \times 10^{-4}$ mol/l, sodium chloride was added so as to adjust the concentration of sodium chloride to 700 ppm.

A treating vessel equipped with a pair of electrodes of ceramic plated with platinum and having an area of 0.21 cm² and an interval of the electrodes of 4 mm was charged with 7 ml of the solution. A direct current having DC voltage of 10 V was applied to the solution for 5 minutes to generate hypochlorous acid. The concentration of hypochlorous acid was 10 ppm.

To the obtained solution of hypochlorous acid, a direct current having DC voltage of 5 V and a current of 0.04 A was applied with repeatedly reversing the positive electrode and the negative electrode at an interval of time of 0.017 second, 1 second, 7.5 seconds, 30 seconds, 1 minute or 2 minutes (Experimental Example 5) by using a reverse circuit, or without reversing the positive electrode and the negative electrode (Comparative Experimental Example 1 ). The change of the concentration of hypochlorous acid was measured with the passage of time. The results are shown in FIG. 3.

Figure 3:
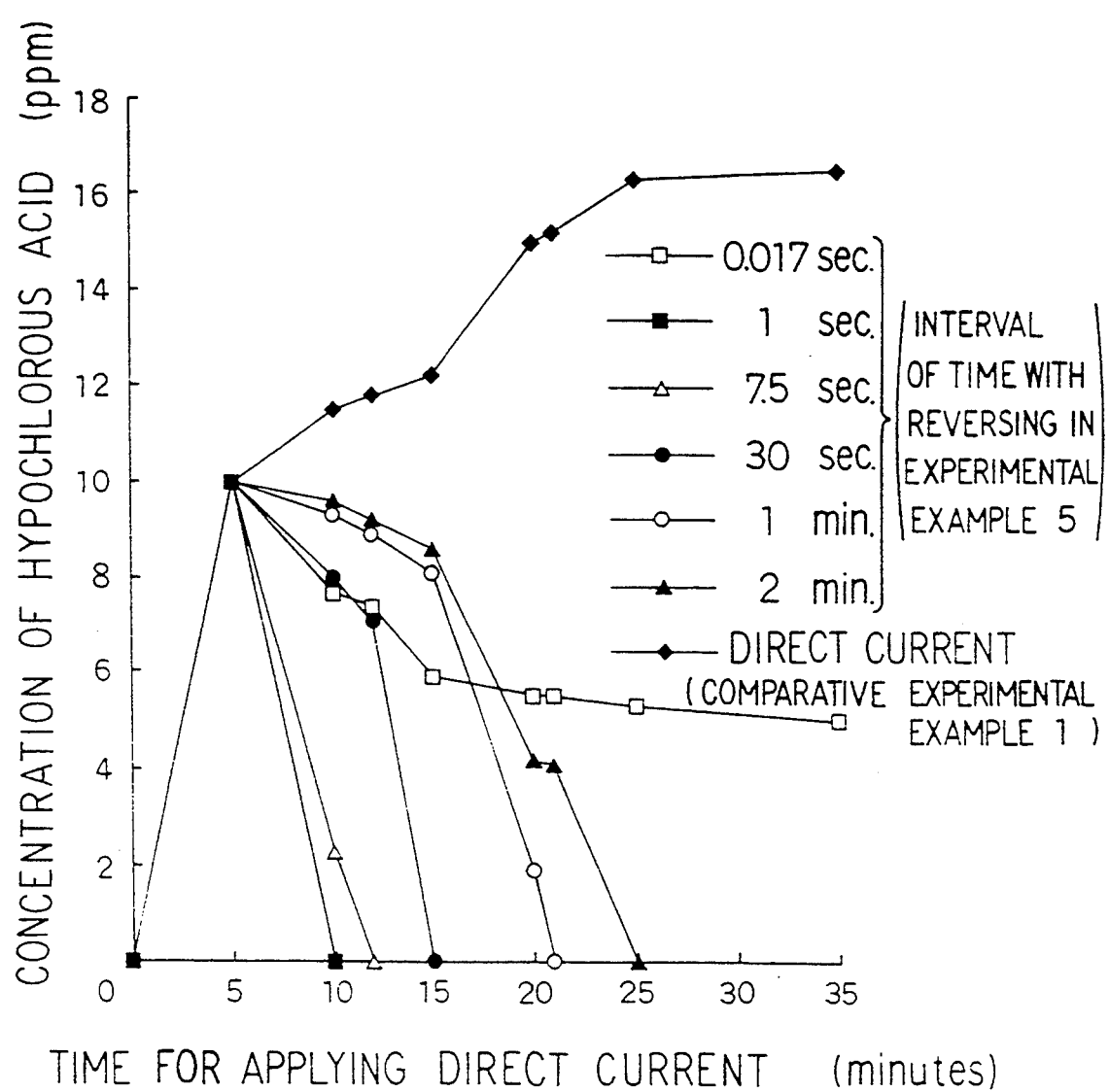
FIG. 3 is a graph showing the relation between time for applying direct current and concentration of hypochlorous acid in the solution containing a halide according to Experimental Example 5 and Comparative Experimental Example 1.

As is clear from the results shown in FIG. 3, it can be seen that hypochlorous acid was reduced in a very short period of time when a direct current was applied to the solution especially with repeatedly reversing the positive electrode and the negative electrode. Also, the most preferable interval of reversing the electrodes was 1 second.

EXPERIMENTAL EXAMPLE 6

Each 7 ml of the solutions for treatment having a concentration of sodium chloride of 300 ppm, 500 ppm or 1000 ppm used in Experimental Example 1 was added to a treating vessel equipped with a pair of electrodes of ceramic plated with platinum and having an area of 0.21 cm² and an interval of the electrodes of 4 mm.

Figure 4:
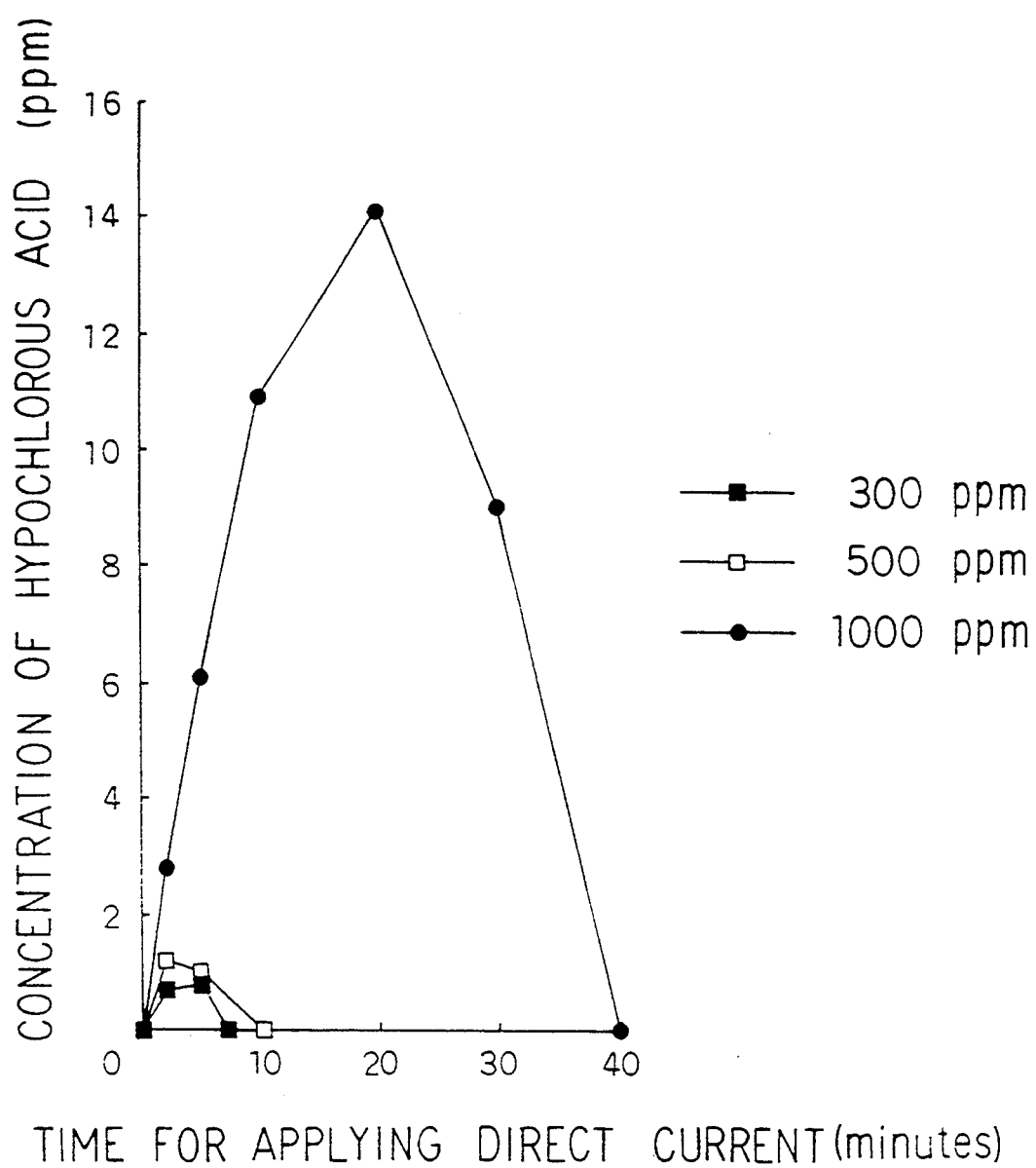
FIG. 4 is a graph showing: the relation between time for applying direct current and concentration of hypochlorous acid in the solution containing a halide according to Experimental Example 6.

To each 7 ml of the solutions for treatment, a direct current having DC voltage of 5 V and a current of 0.04 A was applied with repeatedly reversing the positive electrode and the negative electrode at an interval of time of 7.5 seconds by using a reverse circuit. The change of the concentration of hypochlorous acid was measured with the passage of time. The results are shown in FIG. 4.

As is clear from the results shown in FIG. 4, it can be seen that hypochlorous acid was generated in the early stage, and hypochlorous acid was reduced later in a short period of time with repeatedly reversing the positive electrode and the negative electrode.

EXPERIMENTAL EXAMPLE 7

To a solution of pH 7 containing sodium sulfate in a content of $1.1 \times 10^{-1}$ mol/l, sodium phosphate in a content of $2.4 \times 10^{-4}$ mol/l and disodium phosphate in a content of $3.5 \times 10^{-4}$ mol/l, sodium hypochlorite was added so as to adjust the concentration of hypochlorous acid to 1 ppm, 30 ppm, 50 ppm, 100 ppm, 500 ppm or 1000 ppm.

Each 7 ml of the treating solutions was put into a treating vessel equipped with a pair of electrodes of ceramic plated with platinum and having an area of 0.21 cm$^2$ and an interval of the electrodes of 4 mm.

To each of the treating solutions, a direct current having DC voltage of 10 V and a current of 0.08 A was applied with repeatedly reversing the positive electrode and the netagive electrode at an interval of 2 seconds by using a reverse circuit. The change of the concentration of hypochlorous acid was measured with the passage of time. The results are shown in FIG. 5 except that the concentration of hypochlorous acid was 1 ppm.

Figure 5:
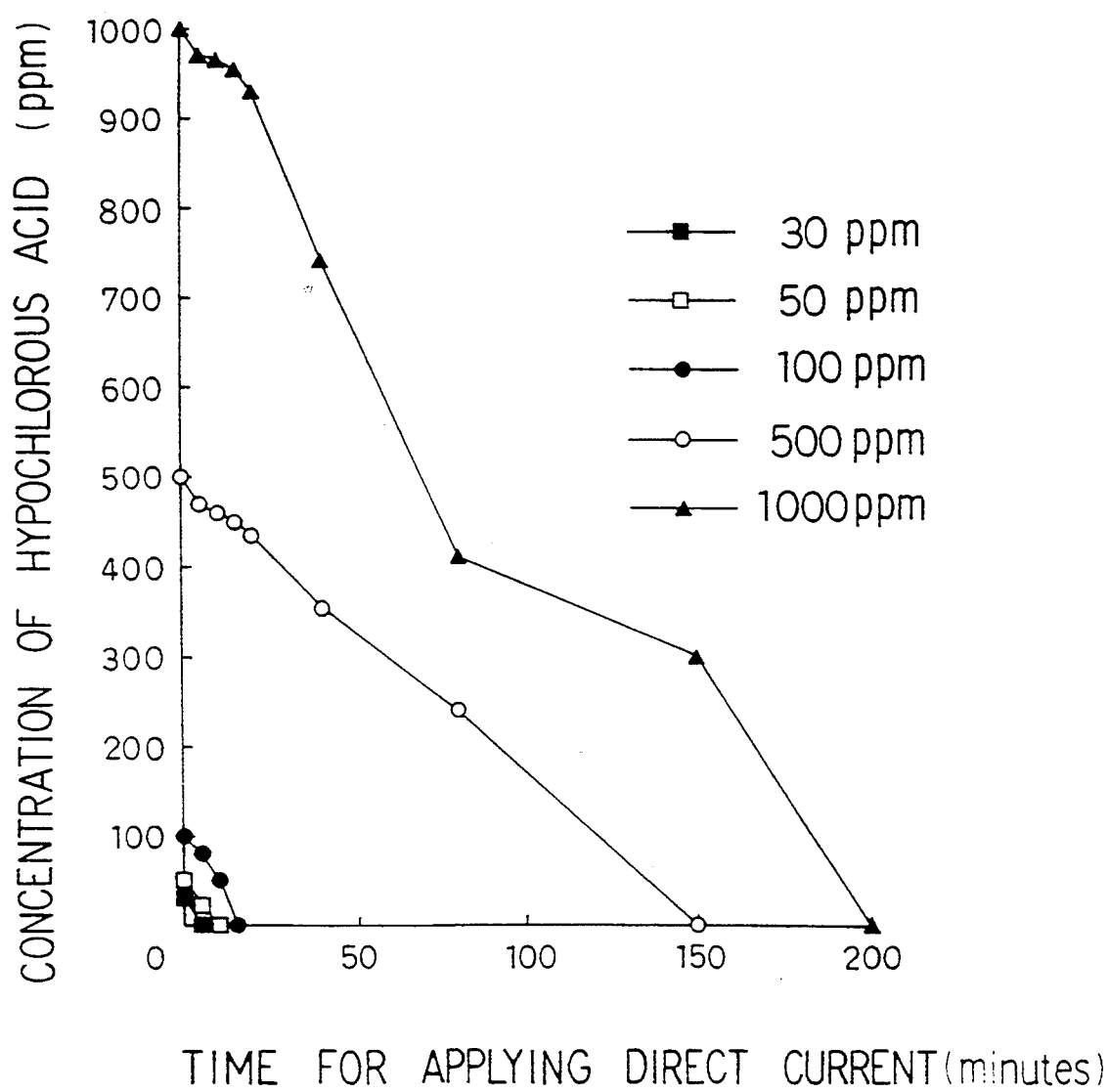
FIG. 5 is a graph showing the relation between time for applying direct current and concentration of hypochlorous acid in the treating solution according to Experimental Example 7.

As is clear from the results shown in FIG. 5, it can be seen that hypochlorous acid was completely reduced when the positive electrode and the negative electrode were repeatedly reversed. Also, it can be seen that hypochlorous acid was reduced in a very short period of time when the concentration of hypochlorous acid was 30 ppm or 50 ppm.

Also, hypochlorous acid was reduced in a very short period of time such as 0.2 minute when the concentration of hypochlorous acid was 1 ppm.

EXPERIMENTAL EXAMPLE 8 to 9

To a solution of pH 7 containing sodium sulfate in a content of $1.1 \times 10^{-1}$ mol/l, sodium phosphate in a content of $2.4 \times 10^{-4}$ mol/l and disodium phosphate in a content of $3.5 \times 10^{-4}$ mol/l, sodium hypochlorite was added so as to adjust the concentration of hypochlorous acid to 30 ppm.

A treating vessel equipped with a pair of electrodes of ceramic plated with platinum and having an area of 0.21 cm$^2$ and an interval of the electrodes of 4 mm was charged with 7 of the treating solution.

To the treating solution, a direct current having DC voltage of 10 V and a current of 0.08 A was applied with repeatedly reversing the positive electrode and the negative electrode at an interval of time of 0.25 second, 0.5 second, 1 second, 2 seconds, 4 seconds, 7.5 seconds or 1 minute in both directions (Experimental Example 8) or at an interval of time of 0.5 second in one direction and 1 second in another direction, at an interval of time of 1 second in one direction and 4 seconds in another direction or at an interval of time of 7.5 seconds in one direction and 1 minute in another direction (Experimental Example 9 ) by using a reverse circuit. The change of the concentration of hypochlorous acid was measured with the passage of time. The results are shown in FIG. 6 (Experimental Example 8) and FIG. 7 (Experimental Example 9).

Figure 6:
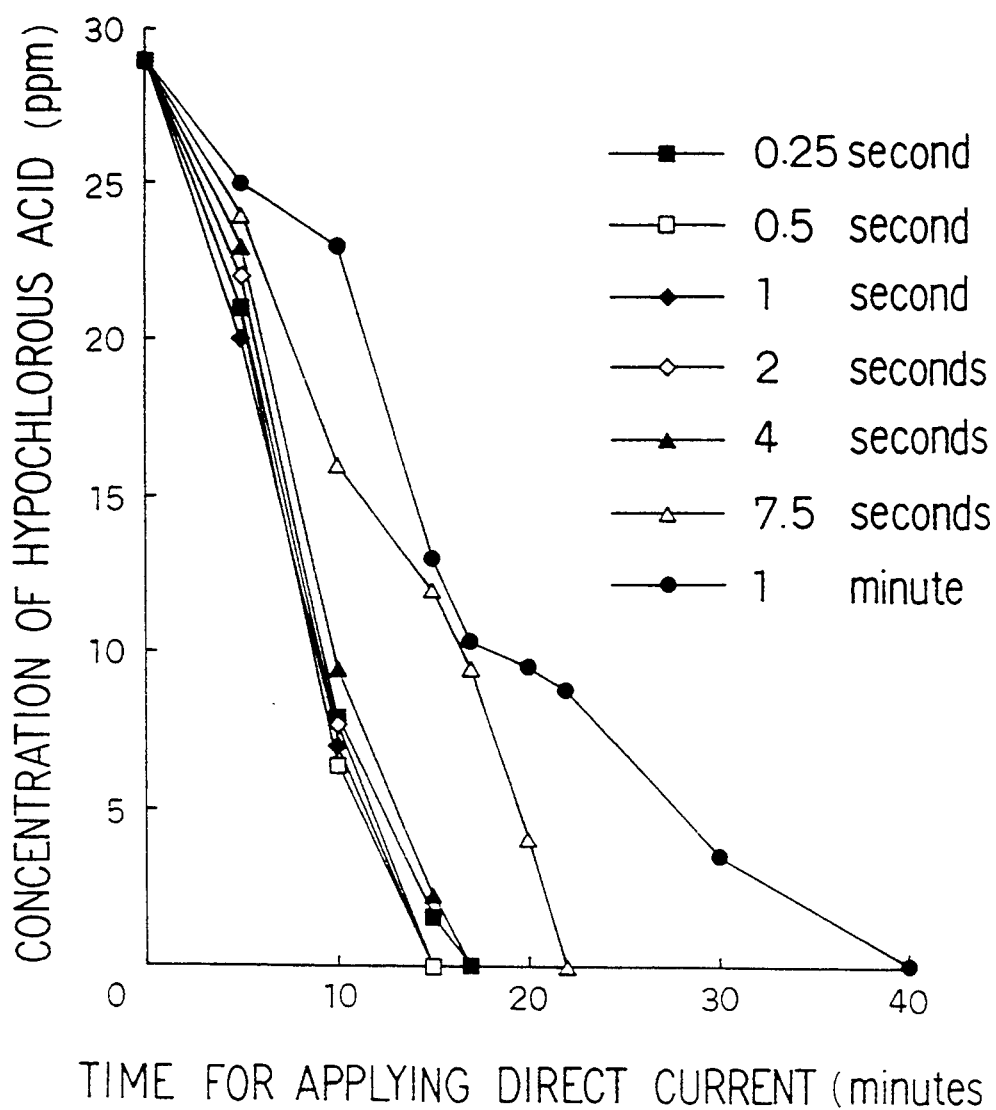
FIG. 6 is a graph showing the relation between time for applying direct current and concentration of hypochlorous acid in the treating solution according to Experimental Example 8.
Figure 7:
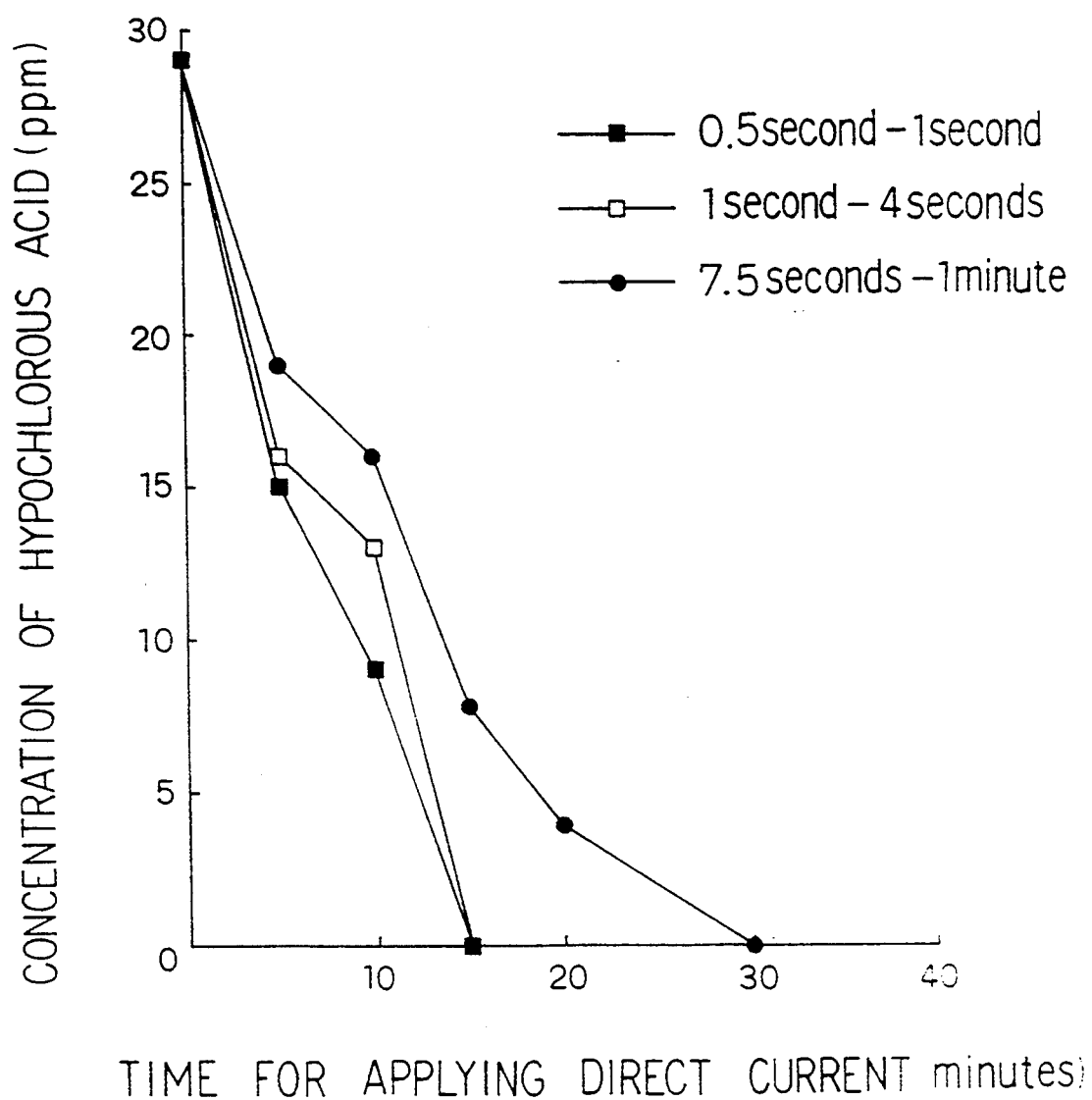
FIG. 7 is a graph showing the relation between time for applying direct current and concentration of hypochlorous acid in the treating solution according to Experimental Example 9.

As is clear from the results shown in FIG. 6 FIG. 7, it can be seen that hypochlorous acid was reduced in a short period of time when the positive electrode and the negative electrode were repeatedly reversed. The preferable intervals of time during reversing were 0.5 second, 1 second or 2 seconds in both directions, or 0.5 second in one direction and 1 second in another direction or 1 second in one direction and 4 seconds in another direction.

COMPARATIVE EXPERIMENTAL EXAMPLES 2 to 3

Each 7 ml of the solutions having a concentration of sodium chloride of 300 ppm or 500 ppm used in Experimental Example 1 was added to a treating vessel equipped with a pair of electrodes of ceramic plated with platinum and having an area of 0.21 cm$^2$ and an interval of the electrodes of 4 mm.

To each of the solutions, a direct current having DC voltage of 5 V and a current of 0.04 A was applied for 5 minutes in one direction and 5 minutes in another direction. The change of the concentration of hypochlorous acid was measured with the passage of time (Comparative Experimental Example 2). The results are shown in FIG. 8.

Also, each 7 ml of the solutions was added to an electrolytic bath separated into two electrolytic rooms by a diaphragm stuck with an ion-exchange membrane. After each of the electrolytic rooms of the electrolytic bath was equipped with an electrode, respectively, a direct current having DC voltage of 10 V and a current of 0.08 A was applied thereto for 5 minutes in one direction and 5 minutes in another direction. The change of the concentration of hypochlorous acid in the electrolytic room having a negative electrode was measured with the passage of time after 5 minutes passed. The results are shown in FIG. 9.

Figure 8:
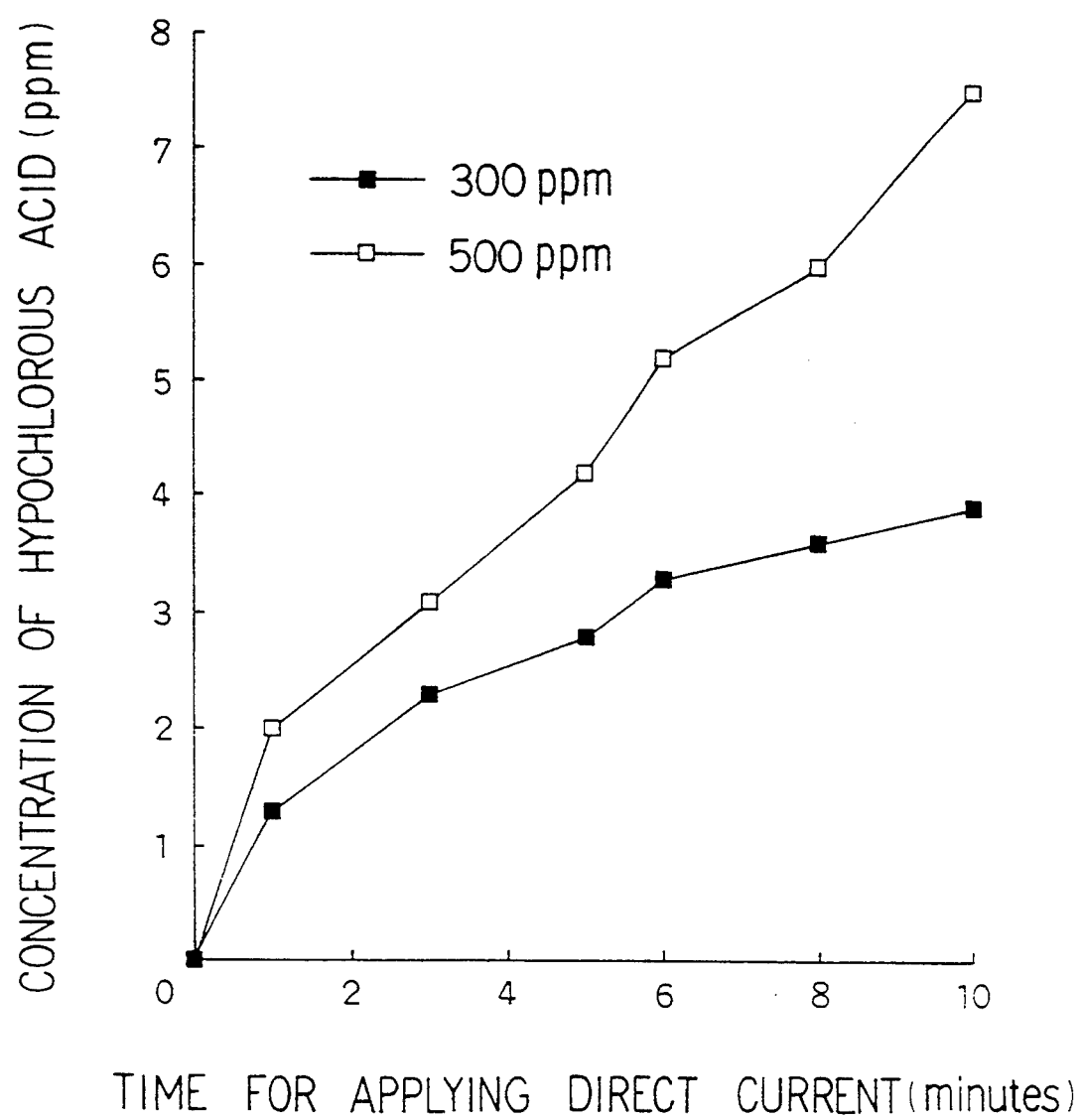
FIG. 8 is a graph showing the relation between time for applying direct current and concentration of hypochlorous acid in the solution containing a halide according to Comparative Experimental Example 2.
Figure 9:
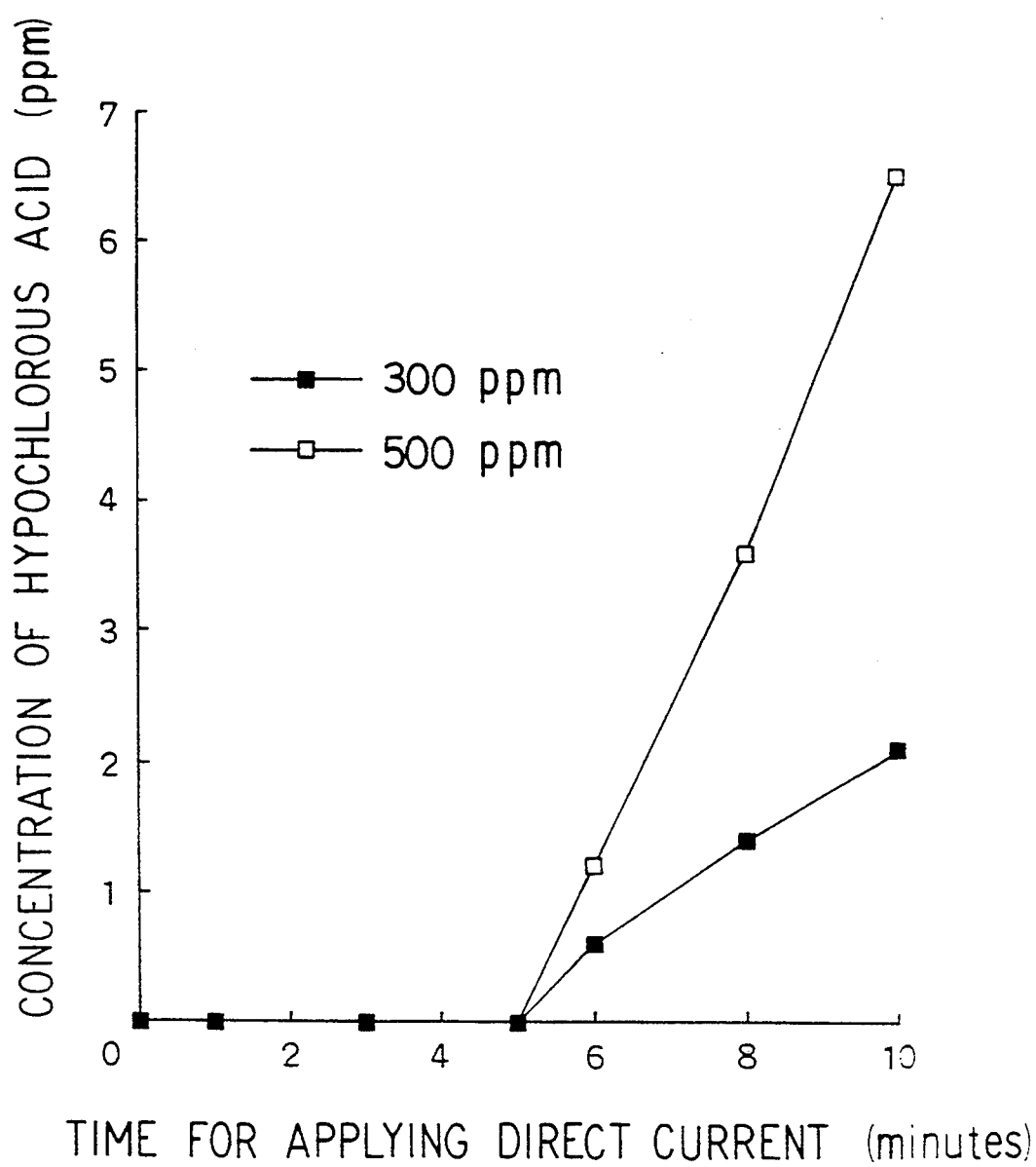
FIG. 9 is a graph showing the relation between time for applying direct current and concentration of hypochlorous acid in the solution containing a halide according to Comparative Experimental Example 3.

As is clear from the results shown in FIG. 8 and FIG. 9, it can be seen that hypochlorous acid was not reduced at all and stably existed in the treating solutions when the electrodes were reversed only one time.

Then, the diaphragm was removed from the electrolytic bath used in Comparative Experimental Example 3 and the treating solutions contained in the electrolytic rooms were mixed together.

When the solution having a concentration of 300 ppm of sodium chloride was used, 1.8 ppm of hypochlorous acid was remained therein. When the solution having a concentration of 500 ppm of sodium chloride was used, 3.2 ppm of hypochlorous acid was remained therein.

From this results, it can be seen that hypochlorous acid was hardly reduced.

EXAMPLES 1 to 7

To a solution of pH 7 containing sodium sulfate in a content of $1.1 \times 10^{-1}$ mol/l, sodium phosphate in a content of $2.4 \times 10^{-4}$ mol/l and disodium phosphate in a content of $3.5 \times 10^{-4}$ mol/l, sodium chloride was added so as to adjust the concentration of sodium chloride to 100 ppm, 150 ppm, 200 ppm, 250 ppm, 400 ppm, 600 ppm or 1000 ppm.

Each 7 ml of the solutions for treatment was put into a treating vessel equipped with a pair of electrodes of ceramic plated with platinum and having an area of 0.21 cm$^2$ and an interval of the electrodes of 4 mm.

Colored soft contact lenses having a water content of 72% by weight and colored in light green, which were commercially available from Menicon Co., Ltd. under the trade name of MENICON SOFT 72, were immersed in the solutions. So as to disinfect the soft contact lenses, a direct current was applied thereto for the time shown in Table 1 by using a dry battery having DC voltage of 9 V to generate hypochlorous acid for disinfection. After that, the resulting hypochlorous acid was reduced by applying a direct current having DC voltage of 9 V and a current of 0.06 A to the solutions for treatment for the time shown in Table 1 with reversing the positive electrode and the negative electrode at an interval of time of 2 seconds. The concentration of hypochlorous acid in the solutions for treatment is shown in Table 1.

TABLE 1

| Ex. No. | Concentration of sodium chloride (ppm) | Time for applying direct current (min.) | | Concentration of hypochlorous acid contained in the solution for treatment with the passage of time of application of direct current (ppm) | | | | | | | |
|---|---|---|---|---|---|---|---|---|---|---|---|
| | | At the time hypochlorous acid was generated | At the time hypochlorous acid was reduced (at the time direct current was applied with reversing) | 1 min. | 2 min. | 3 min. | 4 min. | 5 min. | 6 min. | 9 min. | 10 min. |
| 1 | 100 | 9 | 1 | — | — | 0.3 | — | — | 0.5 | 0.7 | 0 |
| 2 | 150 | 9 | 1 | — | — | 0.6 | — | — | 0.8 | 1.1 | 0 |
| 3 | 200 | 9 | 1 | — | — | 1.1 | — | — | 1.4 | 1.7 | 0 |
| 4 | 250 | 4 | 1 | 1.2 | 1.8 | 2.1 | 2.6 | 0 | — | — | — |
| 5 | 400 | 4 | 2 | 1.5 | 2.5 | 3.2 | 4.3 | 0 | — | — | — |
| 6 | 600 | 3 | 2 | 2.5 | 4.5 | 6.5 | 0 | 0 | — | — | — |
| 7 | 1000 | 2 | 3 | 7.6 | 9.3 | 5.6 | 0 | 0 | — | — | — |

As is clear from the results shown in Table 1, it can be seen that hypochlorous acid in the solutions for treatment was completely reduced in a short period of time such as 1 to 2 minutes from the beginning of application of electric current with reversing.

An o-tolidine hydrochloride solution having a concentration of 0.1% commercially available from KISHIDA CHEMICAL CO., LTD. was diluted 80 times with water. The treated contact lenses were immersed in the obtained diluted solution. The existence of hypochlorous acid in the contact lenses was examined by observing whether the contact lenses were colored in yellow or not.

If hypochlorous acid was existed in a content of at least 0.1 ppm, a contact lens would have been colored in yellow. However, the contact lenses had no change in color at all.

From the result, it can be seen that hypochlorous acid was reduced.

Also, the fading of the contact lenses was not observed, and there was no problem when the contact lenses were worn in eyes as they were.

Next, 7 ml of the solution for treatment obtained in Example 1 was prepared for 6 kinds of microbes described below. Each 0.1 ml of water containing a microbe was added to each solution for treatment, and a disinfecting treatment was carried out in the same manner as in the above. The same treatment as in the above was carried out in Examples 2 to 7.

A test for examining disinfecting properties for the microbes (*Escherichia coli*, IFO 3972; *Pseudomonas aeruginosa*, IFO 13275; *Serratia marcescens*, isolated from a contact lens case; *Staphylococcus aureus*, IFO 13276; *Candida albicans*, IFO 1594; *Aspergillus niger*, IFO 455) was carried out in accordance with a plate dilution method by measuring cell numbers of viable microbes in 1 ml of the treating solution. The results are shown in Table 2. The cell numbers of each of the viable microbes (cells/ml) before applying a direct current were shown in parentheses of Table 2.

As is clear from the results shown in Table 2, it can be seen that the method of the present invention shows excellent disinfecting property since the viable microbes completely disappeared or cell numbers of the viable microbes were extremely reduced in comparison with those before applying a direct current.

EXAMPLES 8 to 14

Sixteen soft contact lenses; mainly composed of N-vinylpyrrolidone having a water content of about 70% by weight were immersed in 1.5 ml of an artificial tear fluid having the following ingredients at 37° C. for 1 hour. (Ingredients of artificial tear fluid)

| | |
|---|---|
| Albumin | 11.64 g |
| γ-Globulin | 4.83 g |
| Lysozyme | 3.6 g |
| NaCl | 9.0 g |
| $CaCl_2.2H_2O$ | 0.15 g |
| $NaH_2PO_4.2H_2O$ | 1.04 g |
| Distilled water | 1.0 l |

Fourteen of the contact lenses immersed in the artificial tear fluid were washed by fingers with MENI CLEAN commercially available from Menicon Co., Ltd. Using the same solutions for treatment and the same treating vessel as used in Examples 1 to 7, every two pieces of the contact lenses were immersed in the solutions for treatment and a direct current having DC voltage of 9 V was applied thereto for the time shown in Table 3.

After that, a direct current having DC voltage of 9 V and a current of 0.06 A was applied for the time shown in Table 3 with reversing a positive electrode and a negative electrode at an interval of time of 2 seconds to carry out the cleaning treatment. The procedure for immersing a contact lens in the artificial tear fluid and cleaning the contact lens is hereinafter referred to as Cycle test A.

After 100 cycles of the Cycle test A were carried out, the contact lens was observed with naked eyes, and its

TABLE 2

| | Cell numbers of viable microbe after applying direct current (cells/ml) | | | | | |
|---|---|---|---|---|---|---|
| Ex. No. | Escherichia coli ($1.9 \times 10^6$) | Pseudomonas aeruginosa ($1.3 \times 10^6$) | Serratia marcescens ($2.5 \times 10^6$) | Staphylococcus aureus ($1.1 \times 10^6$) | Candida albicans ($2.4 \times 10^3$) | Aspergillus niger ($2.2 \times 10^3$) |
| 1 | 0 | 0 | 0 | 0 | 7 | 12 |
| 2 | 0 | 0 | 0 | 0 | 0 | 5 |
| 3 | 0 | 0 | 0 | 0 | 0 | 0 |
| 4 | 5 | 0 | 1 | 0 | 17 | 20 |
| 5 | 0 | 0 | 0 | 0 | 0 | 0 |
| 6 | 0 | 0 | 0 | 0 | 0 | 0 |
| 7 | 0 | 0 | 0 | 0 | 0 | 0 | transparency was evaluated in accordance with the following criteria for evaluation. The results are shown in Table 3.

[Criteria for evaluation]
- A: Obtained contact lens has the same transparency as the contact lens to which the Cycle test A was not carried out.
- B: Obtained contact lens has a little cloudiness in comparison with the contact lens to which the Cycle test A was not carried out.
- C: Obtained contact lens is remarkably clouded.

TABLE 3

| Ex. No. | Concentration of sodium chloride (ppm) | Time for applying direct current (min.) | | Transparency of contact lens after 100 cycles |
|---|---|---|---|---|
| | | At the time hypochlorous acid was generated | At the time hypochlorous acid was reduced (at the time direct current) was applied with revsering) | |
| 8 | 100 | 9 | 1 | A |
| 9 | 150 | 9 | 1 | A |
| 10 | 200 | 9 | 1 | A |
| 11 | 250 | 4 | 1 | A |
| 12 | 400 | 4 | 1 | A |
| 13 | 600 | 3 | 2 | A |
| 14 | 1000 | 2 | 3 | A |

As is clear from the results shown in Table 3, it can be seen that when the Cycle test A was carried out 100 times, the obtained treated contact lens showed excellent transparency, and the removal of proteins was sufficiently carried out. Furthermore, no damage of the contact lenses was observed at all after the Cycle test A was carried out 100 times.

COMPARATIVE EXAMPLE 1

After remained 2 pieces of the contact lenses which were immersed in the artificial tear fluid obtained in Examples 8 to 14 were washed by fingers with MENI CLEAN, tear fluid the contact lenses were disinfected by immersing in 1.5 ml of MENI SOAK disinfecting solution commercially available from Menicon Co., Ltd. and using an apparatus for boiling and disinfecting a contact lens commercially available from Menicon Co., Ltd. under the trade name of MENICON LIZER E.

The procedure of immersing a contact lens in the artificial tear fluid and disinfecting the contact lens is hereinafter referred to as Cycle test B.

It was observed with naked eyes that the above two contact lenses which were disinfected by boiling in the MENICON LIZER E apparatus became cloudy after the Cycle test B of the contact lenses was carried out about 20 times.

Moreover, after the Cycle test B of the contact lenses was carried out 100 times in total, the existence of sulfur derived from proteins and phosphorus derived from calcium phosphate was examined by means of an X-ray microanalyzer in order to investigate the factor which causes the cloudiness of the contact lens. As a result, the peak showing the existence of sulfur was detected.

Accordingly, it is supposed that the cloudiness of the contact lens was caused by proteins, and it can be seen that proteins are accumulated in the contact lens when the treatment method according to the present invention is not carried out. Also, the peak showing the existence of phosphorus was not detected.

EXAMPLE 15 AND COMPARATIVE EXAMPLE 2

After two pieces of contact lenses were immersed in 1.5 ml of the artificial tear fluid at 37° C. for 1 hour and washed by fingers with MENI CLEAN tear fluid in the same manner as in Examples 8 to 14, the contact lenses were immersed in the solution obtained in Example 7 and disinfected by using the MENICON LIZER E apparatus. The two contact lenses were allowed to stand to cool to room temperature.

The above procedure was regarded as one cycle. After the procedure was carried out 50 cycles, when the contact lenses were observed with naked eyes, it was observed that both of the two contact lenses became cloudy after about 20 cycles of the procedure were carried out.

From this, it can be seen that proteins could not be sufficiently removed from the contact lenses by the boiling treatment with MENICON LIZER E apparatus (Comparative Example 2).

After 50 cycles of the procedure were furthermore carried out, one piece of the clowed contact lenses was immersed in the same solution for treatment in the treating vessel as used in Example 7. A direct current having DC voltage of 9 V was applied for 2 minutes to the solution for treatment, and a direct current having DC voltage of 9 V and a current of 0.06 A was applied thereto for 2 minutes with reversing the positive electrode and the negative electrode at an interval of time of 2 seconds. When the contact lens taken out from the solution for treatment was observed with naked eyes, the contact lens returned to transparent (Example 5).

As a result, it can be seen that protein can be removed by the method according to the present invention even if the protein is adhered to the contact lens by its thermal denaturation.

EXAMPLES 16 to 20

The same treating vessel as used in Examples 1 to 7 was charged with the same solution for treatment as used in Experimental Example 5 (Example 16) or Experimental Example 6 (Example 17), or the same treating solution as used in Experimental Example 7 (Example 18) or Experimental Examples 8 to 9 (Examples 19 to 20).

After colored soft contact lenses having a water content of 38% by weight and colored in light blue, which were commercially available from Menicon Co., Ltd. under the trade name of MENICON SOFT MA, were immersed therein, the treatment for applying a direct current was carried out under the same conditions as in each of Experimental Examples.

As a result, hypochlorous acid in the solutions for treatment or the treating solutions was completely reduced likewise each of the above Experimental Examples.

The existence of hypochlorous acid in the obtained contact lenses after treated was examined in the same manner as in Examples 1 to 7. As a result, it can be seen that the contact lenses were not discolored at all, and that hypochlorous acid was reduced.

Also, fading and damage of the contact lens were not observed at all, and there was no problem when the contact lens was worn in eyes as it was.

EXAMPLES 21 to 22

To a solution of pH 7 containing sodium sulfate in a content of $1.1 \times 10^{-1}$ mol/l, sodium phosphate in a content of $2.4 \times 10^{-4}$ mol/l and disodium phosphate in a content of $3.5 \times 10^{-4}$ mol/l, sodium bromide was added so as to adjust the concentration of sodium bromide to 400 ppm (Example 21) or 1000 ppm (Example :22).

Each 7 ml of the solutions for treatment was put into a treating vessel equipped with a pair of electrodes of ceramic plated with platinum and having an area of 0.21 cm$^2$ and an interval of the electrodes of 4 mm.

Colored soft contact lenses having a water content of 72% by weight and colored in light green, which were commercially available from Menicon Co., Ltd. under the trade name of MENICON SOFT 72, were immersed in the solutions for treatment.

After a direct current of 0.06 A was applied to the solutions for treatment for 20 minutes to generate hypobromous acid and disinfect the contact lenses by using a dry battery having DC voltage of 9 V, hypobromous acid was reduced by reversing the positive electrode and the negative electrode at an interval of time of 7.5 seconds. The concentration of hypobromous acid contained in the solutions for treatment are shown in Table 4.

As to Examples 21 and 22, the Cycle test A was carried out 100 times in the same manner as in Examples 8 to 14, each of the obtained contact lenses was evaluated as A. Also, it could not be observed that the color of the lenses was faded.

In addition to the ingredients used in the Examples, other ingredients can be used in the Examples as set forth in the specification to obtain substantially the same results.

What is claimed is:

1. A cleaning and disinfecting method for a contact lens comprising immersing a contact lens in a treating solution containing a hypohalogenous acid and applying a direct current between a pair of electrodes immersed in the treating solution with repeatedly reversing a positive electrode and a negative electrode to reduce said hypohalogenous acid said pair of electrodes being made of ceramic or synthetic resin and coated with platinum.

2. The cleaning and disinfecting method for a contact lens of claim 1, wherein the treating solution containing a hypohalogenous acid is prepared by applying a direct current to a solution containing a halide.

3. The cleaning and disinfecting method for a contact lens of claim 1, wherein the concentration of the hypohalogenous acid in the treating solution is 0.1 to 1000 ppm.

4. The cleaning and disinfecting method for a contact lens of claim 1, wherein the reverse of the positive electrode and the negative electrode is repeatedly carried out at an interval of 0.01 second to 2 minutes.

5. The cleaning and disinfecting method for a contact lens, comprising immersing a contact lens in a solution for treatment containing a halide, applying a direct current between a pair of electrodes immersed in the solution for treatment to generate a hypohalogenous acid, and applying a direct current between the pair of electrodes immersed in the solution for treatment with

TABLE 4

| Ex. No. | Concentration of sodium bromide (ppm) | Concentration of hypobromous acid contained in the solution for treatment with the passage of time of application of direct current (ppm) | | | | |
|---|---|---|---|---|---|---|
| | | 10 minutes | 20 minutes | 30 minutes | 40 minutes | 50 minutes |
| 21 | 400 | 3.2 | 5.1 | 0 | 0 | 0 |
| 22 | 1000 | 23.6 | 43.7 | 31.7 | 15.9 | 0 |

An o-tolidine hydrochloride solution having a concentration of 0.1% was diluted 80 times with water, the treated contact lenses were immersed therein, and it was examined whether the contact lenses were colored in yellow or not. If hypobromous acid was existed in a content of at least 0.1 ppm, a contact lens would have been colored in yellow. However, the contact lenses had no change in color at all. From this, it can be seen that hypobromous acid is reduced even in the contact lenses.

repeatedly reversing a positive electrode and a negative electrode to reduce said hypohalogenous acid.

6. The cleaning and disinfecting method for a contact lens of claim 5, wherein the concentration of the halide in the solution for treatment is 10 to 3000 ppm.

7. The cleaning and disinfecting method for a contact lens of claim 5, wherein the reverse of the positive electrode and the negative electrode is repeatedly carried out at an interval of 0.01 second to 2 minutes.

* * * * *